(12) United States Patent
Pace et al.

(10) Patent No.: US 8,352,638 B2
(45) Date of Patent: *Jan. 8, 2013

(54) SYSTEM FOR NETWORKED DIGITAL PATHOLOGY EXCHANGE

(75) Inventors: Charles P. Pace, North Chittenden, VT (US); Eric W. Wirch, Cambridge, MA (US)

(73) Assignee: Corista, LLC, Concord, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,891

(22) Filed: May 21, 2012

(65) Prior Publication Data

US 2012/0296980 A1    Nov. 22, 2012

Related U.S. Application Data

(63) Continuation of application No. 12/843,138, filed on Jul. 26, 2010, now Pat. No. 8,244,912.

(60) Provisional application No. 61/228,819, filed on Jul. 27, 2009.

(51) Int. Cl.
  *G06F 15/16* (2006.01)
(52) U.S. Cl. .......................... 709/247; 709/249; 382/128
(58) Field of Classification Search .................. 709/204, 709/246, 247, 249; 382/128
See application file for complete search history.

(56) References Cited

U.S. PATENT DOCUMENTS

| | | | |
|---|---|---|---|
| 6,348,793 B1 | 2/2002 | Balloni et al. | |
| 6,661,228 B2 | 12/2003 | Haworth et al. | |
| 6,823,203 B2 | 11/2004 | Jordan | |
| 6,859,513 B2 | 2/2005 | Sako | |
| 6,938,156 B2 * | 8/2005 | Wheeler et al. | 713/170 |
| 6,954,767 B1 | 10/2005 | Kanada | |
| 7,028,182 B1 | 4/2006 | Killcommons | |
| 7,224,839 B2 | 5/2007 | Zeineh | |
| 7,257,268 B2 | 8/2007 | Eichhorn et al. | |
| 7,302,164 B2 | 11/2007 | Wright et al. | |

(Continued)

FOREIGN PATENT DOCUMENTS

EP    1455305 A2 *  9/2004

(Continued)

OTHER PUBLICATIONS

International Search Report and Written Opinion, PCT/US2010/043190, mailing date Feb. 18, 2011.

(Continued)

*Primary Examiner* — Patrice Winder
*Assistant Examiner* — Tauqir Hussain
(74) *Attorney, Agent, or Firm* — Hamilton, Brook, Smith & Reynolds, P.C.

(57) ABSTRACT

A computer-based method and apparatus facilitate exchange of pathology studies enabling primary and secondary pathological diagnoses. A study consists of lower-resolution images, references to the corresponding higher-resolution images, associated image metadata, study metadata and patient metadata. The studies are exchanged from one organization (hospital, practice, or individual physician) to another organization through a set of interconnected dispatcher services. In a cloud model, a plurality of dispatchers may be connected through a Global Dispatcher, both facilitating the addition of new organizations to the cloud and allowing for the addressing of studies from any organization in the cloud to any organization, group or individual in the cloud. Efficiency in diagnosis is improved through the addressing of a study to a plurality of qualified recipients, as the first recipient with an appropriate, available resource may review and provide a diagnosis for the study.

16 Claims, 9 Drawing Sheets

U.S. PATENT DOCUMENTS

| | | | |
|---|---|---|---|
| 7,602,524 B2 | 10/2009 | Eichhorn et al. | |
| 7,738,688 B2 | 6/2010 | Eichhorn et al. | |
| 7,787,674 B2 | 8/2010 | Eichhorn | |
| 7,826,649 B2 | 11/2010 | Crandall et al. | |
| 7,944,478 B2 | 5/2011 | Shiibashi et al. | |
| 8,036,868 B2 | 10/2011 | Zeineh et al. | |
| 8,108,228 B2 | 1/2012 | Maresh et al. | |
| 8,116,547 B2 | 2/2012 | Olson et al. | |
| 8,244,912 B2 | 8/2012 | Pace et al. | |
| 2001/0041991 A1 | 11/2001 | Segal et al. | |
| 2006/0204066 A1 | 9/2006 | Forster et al. | |
| 2006/0274923 A1 | 12/2006 | Forster et al. | |
| 2008/0181472 A1* | 7/2008 | Doi et al. | 382/128 |
| 2008/0273788 A1 | 11/2008 | Soenksen et al. | |
| 2008/0292159 A1 | 11/2008 | Soenksen et al. | |
| 2010/0048159 A1* | 2/2010 | Stenquist | 455/404.1 |
| 2010/0145990 A1 | 6/2010 | Marcus | |
| 2011/0010192 A1 | 1/2011 | Backhaus et al. | |
| 2011/0060766 A1 | 3/2011 | Ehlke et al. | |
| 2011/0158510 A1 | 6/2011 | Aguilar et al. | |
| 2011/0249910 A1 | 10/2011 | Henderson et al. | |
| 2011/0274320 A1 | 11/2011 | Pace et al. | |
| 2012/0002892 A1 | 1/2012 | Eichhorn et al. | |
| 2012/0014576 A1* | 1/2012 | Olson et al. | 382/128 |
| 2012/0068928 A1 | 3/2012 | Bruss et al. | |
| 2012/0069049 A1 | 3/2012 | Howe et al. | |
| 2012/0072452 A1 | 3/2012 | Stratman et al. | |

FOREIGN PATENT DOCUMENTS

| | | |
|---|---|---|
| JP | 2000-295462 A | 10/2000 |
| JP | 2006-130221 A | 5/2006 |
| KR | 2002-0004108 A | 1/2002 |
| KR | 20020004108 | 1/2002 |
| KR | 10-2004-0082047 A | 9/2004 |
| KR | 10-2009-0006295 A | 1/2009 |

OTHER PUBLICATIONS

Notification Concerning Transmittal of International Preliminary Report on Patentability, PCT/US2010/043190, mailing date Feb. 18, 2011.

International Search Report and Written Opinion, International App No. PCT/US2011/037550, dated Jan. 19, 2012.

"Digital Pathology," *Sunquest Information Systems, Inc.*, http://www.sunquestinfo.com/Products/Pages/DigitalPathology.aspx (accessed Mar. 29, 2012).

"Digital Slide Hosting Service," *Aperio Technologies, Inc.* http://www.aperio.com/pathology-services/digital-service-slide-hosting.asp> (accessed Mar. 29, 2012).

"Total Digital Pathology," *Leica Microsystems* http://www.leica-microsystems.com/prodcuts/digital-pathology/manage (accessed Mar. 29, 2012).

* cited by examiner

NODES AND ORGANIZATIONS

REVIEW REQUEST QUEUE

STUDY EXCHANGE BETWEEN ORGANIZATIONS
(COMPONENT BASED)

MESSAGE EXCHANGE FOR A SINGLE CONSUMER REVIEW

MESSAGE EXCHANGE FOR A REVIEW
FROM MULTIPLE OF CONSUMERS

EXAMPLES OF MESSAGE ROUTING PATHS

SYSTEM FOR NETWORKED DIGITAL PATHOLOGY EXCHANGE

RELATED APPLICATION(S)

This application is a continuation of U.S. application Ser. No. 12/843,138, filed on Jul. 26, 2010, which claims the benefit of U.S. Provisional Application No. 61/228,819, filed on Jul. 27, 2009. The entire teachings of the above application(s) are incorporated herein by reference.

FIELD OF THE INVENTION

A method and apparatus to facilitate the exchange of pathology studies for the purpose of providing a primary or secondary pathological diagnosis. A study consists of one or more lower-resolution images, the references to the corresponding higher-resolution images, associated image metadata, study metadata and patient metadata. The studies are exchanged from one organization (hospital, practice, or individual physician) to another organization through a set of interconnected dispatcher services. In a cloud model, a plurality of dispatchers may be connected through a Global Dispatcher, both facilitating the addition of new organizations to the cloud and allowing for the addressing of studies from any organization in the cloud to any organization, group or individual in the cloud. By this means, the originating organization may obtain the desired level of care through the selection of recipient organizations, groups and individuals according to the organization's existing criteria. Efficiency in diagnosis is improved through the addressing of a study to a plurality of qualified recipients, as the first recipient with an appropriate, available resource may review and provide a diagnosis for the study.

BACKGROUND OF THE INVENTION

The field of Digital Pathology has been recently experiencing an accelerating growth, and its associated technology is moving toward widespread adoption. The resulting efficiencies include reduction in cost, time, and management overhead associated with traditional Pathology services. The reduction in distribution of glass slides between in-house physicians and external physicians performing second opinions or referrals is central to the increase in efficiency. Additionally, other associated activities, including searching for slides for publications and presentations are made more efficient when the digital form's acquisition and distribution are performed digitally rather than physically. Logistical efficiencies in the workflow of slide production, digitization and immediate archival can relieve the already overburdened health care facilities and provide a multitude of additional capacity and services as well. Finally, as there is no single physical piece of media to be viewed, an individual image or study can be accessed simultaneously by multiple local or remote users.

At the time of this filing, there are five characteristic Digital Pathology scenarios that serve to clearly define how Digital Pathology is being deployed and planned. These five scenarios are: Stand Alone Organizations, Expanding Primary Opinion Networks, Point-to-Point Second Opinion Networks, Peer Networks, and Cloud Networks. The Stand Alone scenario is primarily concerned with the intra-organization efficiencies of digitizing slides and archiving slides for in house pathology services. In the Expanding scenario, the health facility is looking to augment or outsource their own pathology services to a second organization, facility or expert center offering external pathology services, possibly obviating the requirement for intra-organizational pathology services, and leveraging the Digital Pathology System of the second organization. The Point-to-Point scenario is a dedicated second opinion or subspecialty service provided by a second organization to a first organization, where the first organization still maintains its own Digital Pathology System. The Peer-base scenario defines two or more organizations that leverage each of their Digital Pathology services to provide both combined primary and direct secondary pathology services to both organizations. The Cloud Network scenario is more of a speculative scenario where global pathology services can be leveraged by an organization in order to leverage efficiencies of scale without a direct linear relationship of that scaling to cost.

Stand Alone Organizations

For a digital pathology solution inside of an organization (Inside an organization does not denote network topology as much as all personnel accessing the digital pathology system have network credentials and can access the system either directly or through existing hospital security infrastructure) digital pathology applications (including triage, reports generation and primary diagnostic viewing) can be achieved through a direct connection to the deployed metadata & imaging services (see Architecture 1). In this case, because the pathologist is directly related to the organization requesting the diagnosis, the pathologist would have access to all of the patient data available via the metadata services, so no summarization, reduction or filtering of metadata is required. Also, because of the low utilization (an image is likely to be triaged, diagnosed and reported only once), caching or generation of preview images (a low- or mid-resolution image to be used during the triage, assignment and reporting processes) for some stages of the workflow are not necessary.

Expanding Primary Opinion Networks

In many remote areas of both the United States and the rest of the world, Pathology Service is still provided by travelling pathologists who cover a group of associated or independent hospitals by travelling between them. In this instance, the highest priced resource in the network is being moved from point-to-point through the network, with significant portions of their time being consumed by travel. Alternatives are to ship the slides to be read to a hospital with pathology services. The downside of this method is that slides are often lost or broken in the two-way transit from source to pathology resource, and this does not provide for rapid diagnostic ability. Extending the bounds of a pathology department's primary diagnostic ability to include remote hospitals that are either under-staffed or do not have the proper specialties is the next major arena for networked pathology.

Image previews first come into play in the case where remote digitizers are deployed to affiliated hospitals where no primary pathology service exists, the primary organization is performing the primary diagnostic service, expanding the effective footprint for the primary organization. In this case, all of the metadata and patient details are entered (or imported) into the primary organization's metadata services, as this is the primary patient record for the pathology system. The images, which exist at the remote location, will have a preview image created (which will be cached at the primary organization) for the triage, assignment and reporting processes. Only during the actual primary diagnosis of the image will the full resolution images be accessed from the remote site.

Point-to-Point Second Opinion Networks

The easy first step towards a networked telepathology solution is the addition of a dependent second organization to provide second opinions on cases. The metadata and image data are retrieved in the same manner as with a primary organization's diagnosis, and the nature of the dependent second organization (a dependent secondary organization does not require any hardware or software to enable their diagnostic abilities, thus they do not have a hardware of software footprint to which info can be cached) does not require or provide an efficient opportunity to cache either a preview image or metadata that would represent a lower-cost (from a network consumption perspective) solution than fetching the data directly from the primary organization's system as needed. This methodology is equivalent to providing limited network credentials and/or providing point-to-point secure network access to any person or organization providing second opinions to the primary institution.

Once the scope of a pathology solution expands beyond the bounds of a single organization with a single physical footprint, some level of data and/or image caching can be effective in reducing server load and bandwidth required to deploy an effective digital pathology system.

Peer Networks

A Peer Network scenario differs from the Primary/Dependent scenario by the fact that both organizations have a networked digital pathology system, and those systems can exchange studies. Cached metadata become useful and, coupled with a preview image, form a package which can be forwarded to a stand-alone peer system at a second organization. The first architecture requiring the forwarding of packages is the peer organization model, where two organizations (each is an independent organization with their own digital pathology solution) can be directly connected to one another and exchange studies (a package consisting of preview images, the study-specific metadata and security tokens for accessing the full image) for second opinions or consultation. Directly connecting the two organizations involves establishing network links and exchanging security certificates, and allows for the trusted exchange of information. Once connected, studies are directly assigned from one organization to another, and the queue of studies to be processed is the combination of all studies from the primary organization and all studies which have been referred to it by peer organization(s).

Cloud Networks

The evolution of networked pathology services is the cloud model. In the cloud model, studies are not directly assigned to an organization, but instead are made available to a specified group of recipients for second opinion. In the cloud model, the package is similarly made up of preview images, study-specific metadata and, instead of security tokens, a list of authorized recipients. The recipients may represent individual doctors, well known groups of doctors or other organizations. When a member of the recipient list views and accepts the study, that recipient has claimed the study and it is no longer available to the other recipients (first come, first served). This provides the quickest possible diagnosis for the study from the list of acceptable organizations and individuals, and will lead to the creation of 'expert groups'.

SUMMARY OF THE INVENTION

The invention facilitates the exchange of studies (FIG. 1-105) between two or more organizations (FIG. 2, element 230), each potentially with their own digital pathology systems. Each study may consist of one or more digital pathology images and associated metadata, as well as patient metadata. When multiple organizations are networked, studies co-exist in a physicians work queue from both the physician's own organization and from secondary organizations (FIG. 3-Review Request Queue).

The invention processes Study Review Requests to generate Study Reviews via a federated system of edge and dispatch nodes. Dispatch nodes are utilized to route a large numbers of study review requests over constrained networking infrastructure with decreased requirements for bandwidth and minimal user intervention. The invention further defines a means of addressing, routing, and transactional queue management relating to the exchange of studies.

In one preferred embodiment, the Simple Distribution Process, the initial Study Review Request is generated by the Originating Node, and is sent to the Consuming Node, indicating the presence of an available study on the Originating Node.

This embodiment is a computer-based method of distributing biological sample data based on specified study review criteria, both of which are on the Originating Node. On the Originating Node, a Study is generated based on the specified study review criteria. Further, a progressive transmission is prepared. The progressive transmission is based on transmission of requested subsets of biological sample data, thereby not requiring the whole of the data to be transmitted. Additionally, based on the specified study review criteria, a Study Review Request is prepared. The review request is then transmitted to at least one Consuming Node. In response to a signal from the Consuming Node, the transmission is streamed in a progressive manner, as a subset, in part or in full, from the Originating Node to the Consuming Node. These subsets are based on the progressive technique employed, and would include the following non-limiting aspects: spatial regions, scale, tiling, or other common progressive image transmission techniques.

In a second preferred embodiment, the Dispatched Distribution Process, the initial Study Review Request is generated by the Originating Node, and is sent to a Dispatcher Node, which forwards the communications to the Consuming Node.

This embodiment is a computer-based method of distributing biological sample data based on specified study review criteria, both of which are on the Originating Node. On the Originating Node, a Study is generated based on the specified study review criteria. Further, a progressive transmission is prepared. The progressive transmission is based on transmission of requested subsets of biological sample data, thereby not requiring the whole of the data to be transmitted. Additionally, based on the specified study review criteria, a Study Review Request is prepared. The review request is then transmitted to at least one Dispatcher Node. The Study Review Request is then forwarded from the Dispatcher Node to a Consuming Node. In response to a signal from the Consuming Node, which is sent to the Dispatcher Node and forwarded to the Originating Node, the transmission is sent in a progressive manner, as a subset, in part or in full, from the Originating Node to the Consuming Node via the Dispatcher. These subsets are based on the progressive technique employed, and would include the following non-limiting aspects: spatial regions, scale, tiling, or other common progressive image transmission techniques.

BRIEF DESCRIPTION OF FIGURES

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 shows the Data Structures in the Exchange of Studies. There are six major data types, composed of two studies (105), which are equivalently known as packages, a Study Review Request (130), Study Review Acceptance (140) and Study Review Cancellation (150), and a Study Review (160).

The first package type is a Preview Study (110). The first element of the preview study is Preview Study Metadata (111), which includes filtered or restricted notes of the originator of the study. The second element is Restricted Patient Metadata (112), which is comprised of anonymized patient metadata. The third element is Low-Resolution Images (113) of the Biological Specimen.

The second package type is a Detailed Study (120). The first element of the detailed study is Study Metadata (121), which includes the full (unrestricted) notes of the originator of the study. The second element is Patient Metadata (122), which is comprised of the full (unrestricted) patient metadata. The third element is Additional References (123), which may include references to additional patient metadata, such as the patient's EMR (Electronic Medical Record) or similar cases, comparable images or notes which are not specifically from this patient or study. The fourth element is Multi-Resolution Images (114) of the Biological Specimen, which includes zoom-able, progressive access to the Whole Slide Image (equivalently WSI) at different image resolutions (equivalently, zoom levels).

The next data structure is the Study Review Request (130), which is sent from the Originator to the Consumer. The first element of the review request is a Preview Study (110). The second element is a Detailed Study Reference (131), which provides the necessary information to access the detailed study. The third element is the Recipient List & Policies (132), which includes study priority, expiration, cardinality, routing information or other policy details.

The fourth data structure is the Study Review Acceptance (140). This message is sent in response to the review request (130), and notifies the originator of the review request of the consumer's acceptance or rejection of the Study Review Request.

The fifth data structure is the Study Review Cancellation (150). This message is sent to consumers in the event of a manual review cancellation by the originator, due to a Study Review Request's expiration, or due to the review request meeting its conditions by other consumers.

The sixth data structure is the Study Review (160). The first element is a Pathology Review (161), which includes text, verbal or other notes and diagnosis from the Consumer. The second element is Pathology Review Metadata (162), which may include details of the pathology review session, measurements or other data. The third element is Pathology Review Annotations (163), which may include notes and a point or region based annotation at a specific location (location and resolution) of a Multi-Resolution Image (114). The fourth element is Pathology Review Sub-Images or External Reference Images (164), which may contain sub-images from the Multi-Resolution Images (114) of the detailed study, or references to images outside of the study which are comparable or supportive of the Pathology Review.

FIG. 2

Figure 2:
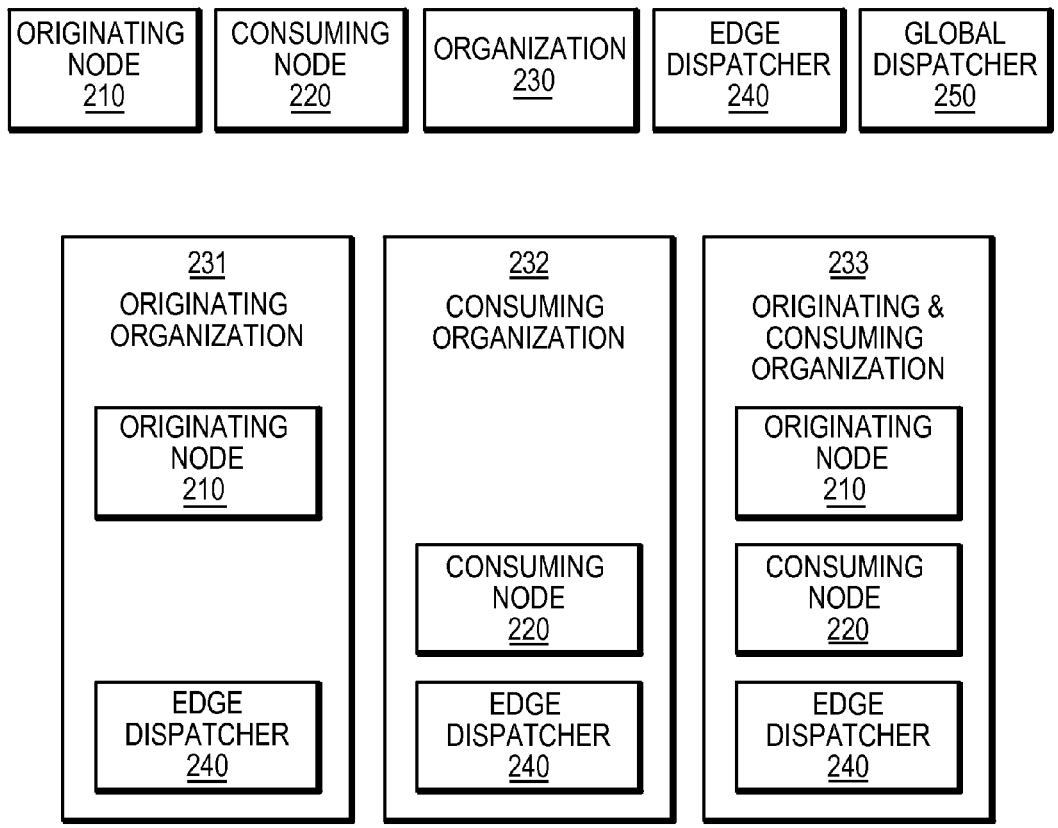

FIG. 2 depicts the node, organizations and router types in a digital pathology system, and the organization configurations which can be created using those node and routers. The first node type is an Originating Node (210), equivalently referred to as the Originating User or Originator Node, which creates packages (105) and Study Review Requests (130). The second node type is a Consuming Node (220), equivalently referred to as a Target User or Consumer Node, for which a review request is assembled and assigned, and which generates a Study Review (140) which is returned to the Originator.

An Organization (230) is a grouping of one or more Originating Nodes (210), Consuming Nodes (220) and an Edge Dispatcher (240). An organization represents a logical entity which produces, consumes or both produces and consumes packages.

The first of the two router types is an Edge Dispatcher (240). The Edge Dispatcher is responsible for routing the package (105) from the Originating Node (210) to the Consuming Node (220). In the simplest of embodiments, both of nodes and the edge dispatcher exist within the same Organization, and may be the same User. The second router type is the Global Dispatcher (250), which is used to route and federate packages (105) between organizations (230). The edge dispatcher of the originating organization will route a package through a global dispatcher to the edge dispatcher of the consuming organization.

The various Nodes and Edge Dispatchers can be combined into a set of different organization. The first example organization is an Originating Organization (231), which contains one or more Originating Nodes (210) and an Edge Dispatcher (240). This second example organization is a Consuming Organization (232), which contains one or more Consuming Nodes (220) and an Edge Dispatcher (240). The final example organization is an Originating and Consuming Organization (233), which contains one or more Originating Nodes (210), one or more Consuming Nodes (220) and an Edge Dispatcher (240).

FIG. 3

Figure 3:
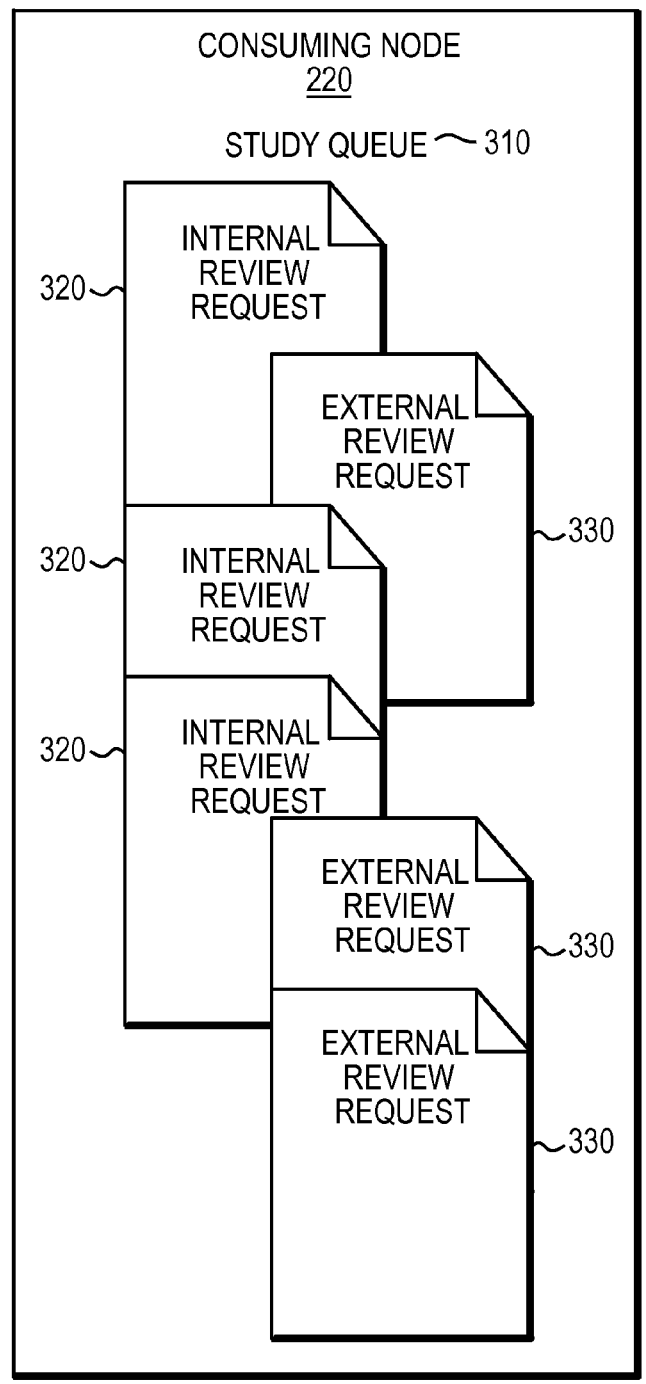

FIG. 3 depicts the Study Queue of an Organization. In an organization with a Consuming Node (210), there is a Study Work Queue (310). The study work queue contains both Internal Study Review Requests (320) and External Study Review Requests (330). An internal Study Review Request is a review request which is generated within the same organization as the consuming node. An external Study Review Request is a review request which is generated by a different organization from the consuming node.

FIG. 4

Figure 4:
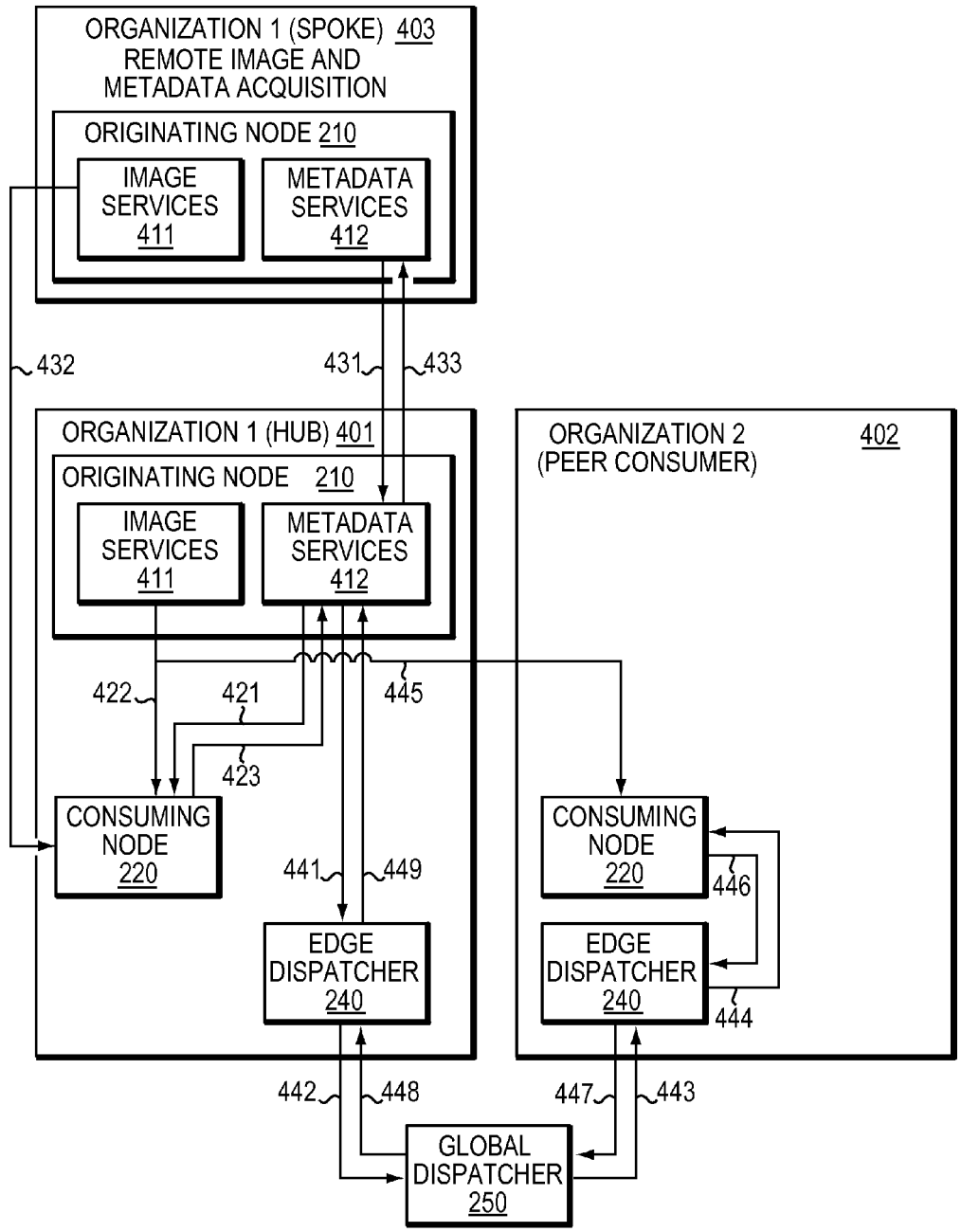

FIG. 4 is an overview of the major components required to process Studies (both Preview Studies and Detailed Studies) from a) an organization to itself, b) from a consumer only site, c) to a peer organizations through a global dispatcher.

In the first embodiment, a Review Request is generated within an Organization (401) which is an Originating and Consuming Organization (233), containing an Originating Node (210), a Consuming Node (220), and an Edge Dispatcher (240). The Originating Node is comprised of both Image Services (411) and Metadata Services (412). First, a Study Review Request (130) is sent from the Originating Node's Metadata Services to the Consuming Node (421). A Study Review Acceptance (140) message is sent from the Consumer to the Image Services (423). The Consumer has access to the Detailed Study (120) images from the Image Services (422), and the metadata from the Metadata Services (421). Finally, a Study Review (160) is sent from the Consumer to the Originator's Metadata Services.

In the second embodiment, a Study Review Request is generated from an organization that provides remote metadata and image acquisition for the originating organization. The remote Organization (403), which contains an Originating Node (210), creates studies for review by an Organization (401), which is an Originating and Consuming Organization (233), and contains an Originating Node (210), a Consuming Node (220), and an Edge Dispatcher (240). The Originating Node is comprised of both Image Services (411) and Metadata Services (412). First, a Study Review Request (130) is sent from the Originating Node's Metadata Services to the Consuming Node's Metadata Services (431). The Consuming Node can then access the Study Review Request directly from their local Metadata Services (421). A Study Review Acceptance (140) message is sent from the Consumer to the Image Services (423), which is forwarded to the Originator's Metadata Services (433). The Consumer has access to the Detailed Study (120) images directly from the Image Services (432) of the Originating Node, and the metadata from the Metadata Services (421). Finally, a Study Review (160) is sent from the Consumer to the Originator's Metadata Services (433) via the Consumer's local Metadata Services (423).

In the second embodiment, a Study Review Request is generated from an organization that provides remote metadata and image acquisition for the originating organization. The remote Organization (403), which contains an Originating Node (210), creates studies for review by an Organization (401), which is an Originating and Consuming Organization (233), and contains an Originating Node (210), a Consuming Node (220), and an Edge Dispatcher (240). The Originating Node is comprised of both Image Services (411) and Metadata Services (412). First, a Study Review Request (130) is sent from the Originating Node's Metadata Services to the Consuming Node's Metadata Services (431). The Consuming Node can then access the Review Request directly from their local Metadata Services (421). A Study Review Acceptance (140) message is sent from the Consumer to the Image Services (423), which is forwarded to the Originator's Metadata Services (433). The Consumer has access to the Detailed Study (120) images directly from the Image Services (432) of the Originating Node, and the metadata from the Metadata Services (421). Finally, a Study Review (160) is sent from the Consumer to the Originator's Metadata Services (433) via the Consumer's local Metadata Services (423).

In the third embodiment, a Study Review Request is generated from an Originating and Consuming Organization (401) to a peer Consuming Organization (403). A Study Review Request is sent from the Originating Organization to the Consuming Organization. This message is routed (441) from the Metadata Services (412) through the Originator's Edge Dispatcher, which is then routed (442) to the Global dispatcher, which is then routed (443) to the Consumer's Edge Dispatcher, which is then routed (444) to the Consuming Node. The Study Review Acceptance message is then routed from the Consuming Node to the Edge Dispatcher (446), then to the Global Dispatcher (447), then to the Originator's Edge Dispatcher (448), before being routed to the Originating Node (449). The Detailed Study (120) image access is direct (445) from the Image Services (411), with the Detailed Study metadata coming via the Edge and Global Dispatchers (441-442-443-444). Finally, the Study Review (160) is routed from the Consuming Node to the Originating Node via the Edge and Global Dispatchers (446-447-448-449).

FIG. 5

Figure 5:
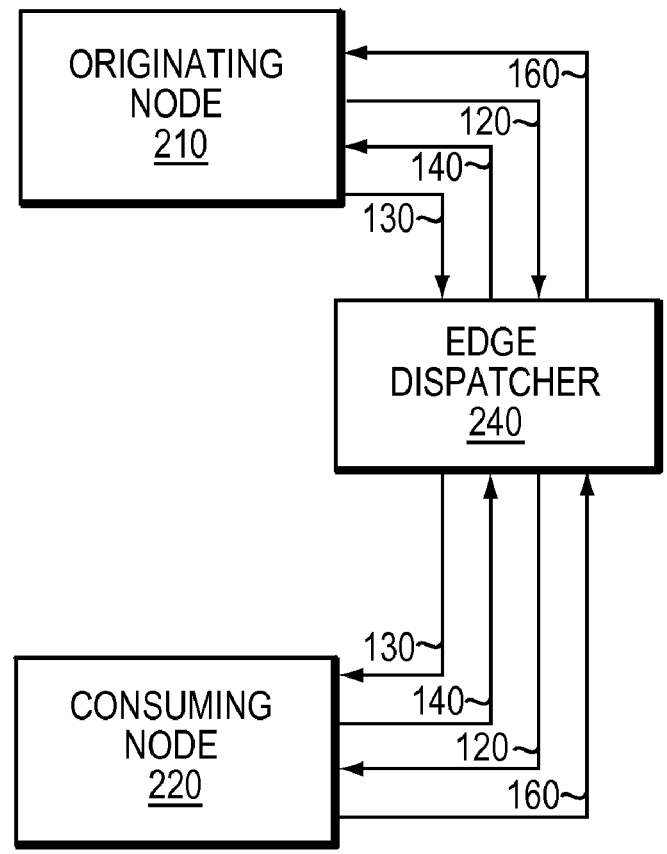

FIG. 5 depicts the Message Exchange for a Single Consumer Review. A single consumer review involves a single Originating Node (210), a single Consuming Node (220), and a single Edge Dispatcher (240).

Initially, the Originating Node (210) assembles a Preview Study (110) and a Detailed Study (120). It then packages the Preview Study and a reference to the Detailed Study into a Study Review Request (130), which is sent to the Consuming Node (220) via the Edge Dispatcher (240). The Consuming Node receives the Review Request, evaluates it, and sends a Study Review Acceptance (140) message back to the Originator via the Edge Dispatcher, designating the Study as accepted, and the Consuming Node as the Assigned Node. At this point, the Consuming Node has access to the Detailed Study (120) via the Edge Dispatcher. Finally, upon completion of the Consuming Node's review, the Consuming Node submits its Study Review (160) to the Originator, via the Edge Dispatcher.

FIG. 6

Figure 6:
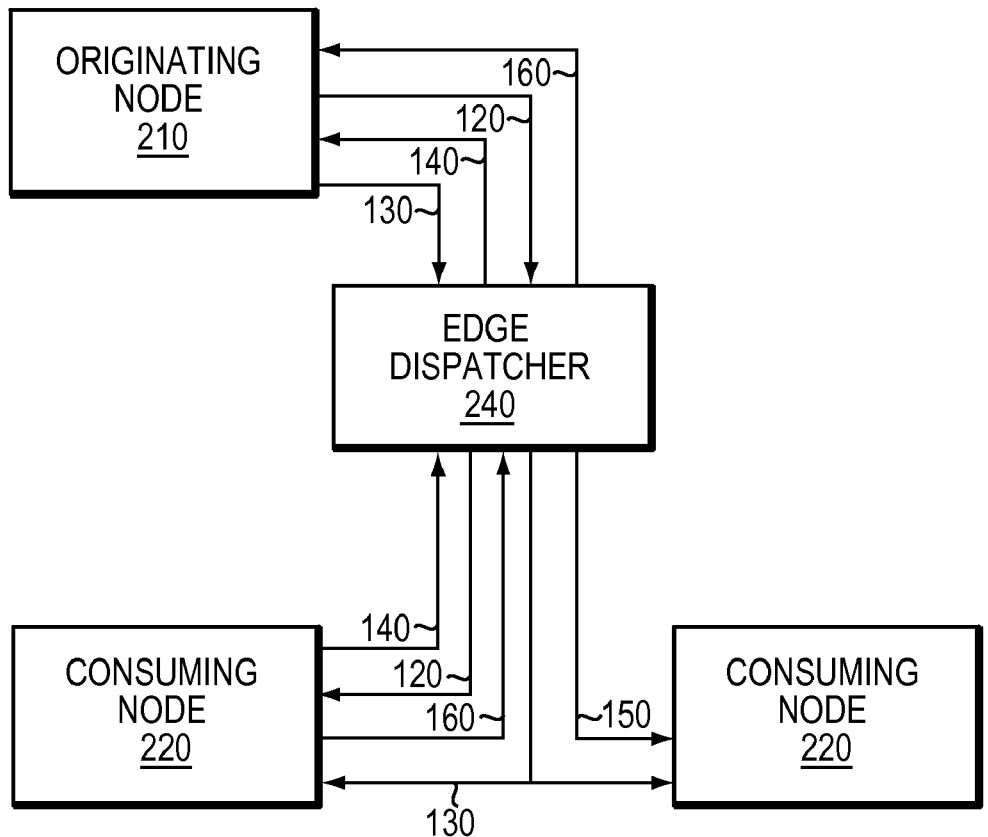

FIG. 6 depicts the Message Exchange for a Review from Multiple Consumers. A multi-consumer review involves a single Originating Node (210), two or more Consuming Nodes (220), and a single Edge Dispatcher (240).

Initially, the Originating Node (210) assembles a Preview Study (110) and a Detailed Study (120). It then packages the Preview Study and a reference to the Detailed Study into a Study Review Request (130), which is sent to all Consuming Nodes (220) via the Edge Dispatcher (240). Each Consuming Node receives the Review Request and has the opportunity to evaluate it. The first Consuming Node to evaluate the review request and send a Study Review Acceptance (140) message back to the Originator via the Edge Dispatcher is designated the Assigned Node, and the Study is deemed Accepted. If the Cardinality of the Study Review Request has been met, a Study Review Cancellation (150) message is sent to the remainder of the Consuming Nodes. At this point, the Consuming Node which has accepted the study has access to the Detailed Study (120) via the Edge Dispatcher. Finally, upon completion of the Consuming Node's review, the Consuming Node submits its Study Review (160) to the Originator, via the Edge Dispatcher.

FIG. 7

Figure 7:
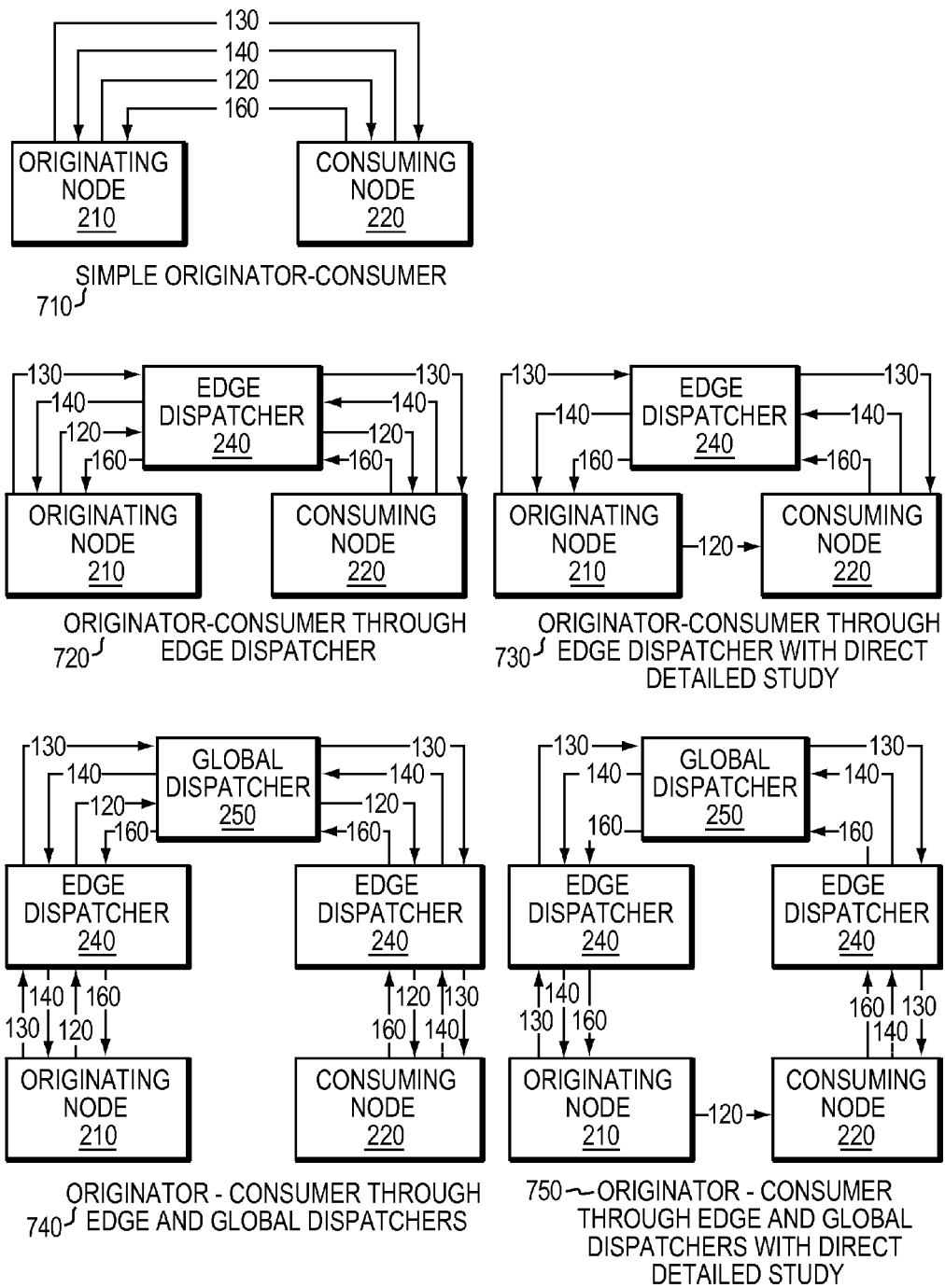

FIG. 7 depicts Embodiments of Messaging Routing Paths, which is a non-limiting example of routing configurations between a single Originating Node (210) and a single Consuming Node (220).

In the first example, Simple Originator-Consumer (710), a Study Review Request (130) is generated and sent from the Originating Node (210) directly to the Consuming Node (220). The Consuming Node responds with a Study Review Acceptance (150) message to the Originating Node. The Consuming Node then has direct access to the Detailed Study (120) from the Originator. Finally, the Consuming Node responds to the Originating Node with a Study Review (160).

In the second example, Originator-Consumer through Edge Dispatcher (720), a Study Review Request (130) is generated and sent from the Originating Node (210) to the Consuming Node (220) via an Edge Dispatcher (240). The Consuming Node responds with a Study Review Acceptance (150) message to the Originating Node via an Edge Dispatcher. The Consuming Node then has access to the Detailed Study (120) from the Originator via an Edge Dispatcher. Finally, the Consuming Node responds to the Originating Node with a Study Review (160) via an Edge Dispatcher.

In the third example, Originator-Consumer through Edge Dispatcher with Direct Detailed Study (730), a Study Review Request (130) is generated and sent from the Originating Node (210) to the Consuming Node (220) via an Edge Dispatcher (240). The Consuming Node responds with a Study Review Acceptance (150) message to the Originating Node via an Edge Dispatcher. The Consuming Node then has direct access to the Detailed Study (120) from the Originator. Finally, the Consuming Node responds to the Originating Node with a Study Review (160) via an Edge Dispatcher.

In the fourth example, Originator-Consumer through Edge and Global Dispatchers (740), a Study Review Request (130) is generated and sent from the Originating Node (210) to the Consuming Node (220) via an Edge Dispatcher (240) associated with the Originator, a Global Dispatcher (250), and a second Edge Dispatcher (240) associated with the Consumer. The Consuming Node responds with a Study Review Acceptance (150) message to the Originating Node via its associated Edge Dispatcher, through the Global Dispatcher, and through the Originator's Edge Dispatcher. The Consuming Node then has access to the Detailed Study (120) from the Originator via both Edge Dispatchers and the Global Dispatcher. Finally, the Consuming Node responds to the Originating Node with a Study Review (160), first through its Edge Dispatcher, the Global Dispatcher, and finally through the Originator's Edge Dispatcher.

In the fifth example, Originator-Consumer through Edge and Global Dispatchers (740), a Study Review Request (130) is generated and sent from the Originating Node (210) to the Consuming Node (220) via an Edge Dispatcher (240) associated with the Originator, a Global Dispatcher (250), and a second Edge Dispatcher (240) associated with the Consumer. The Consuming Node responds with a Study Review Acceptance (150) message to the Originating Node via its associated Edge Dispatcher, through the Global Dispatcher, and through the Originator's Edge Dispatcher. The Consuming Node then has access to the Detailed Study (120) directly from the Originator. Finally, the Consuming Node responds to the Originating Node with a Study Review (160), first through its Edge Dispatcher, the Global Dispatcher, and finally through the Originator's Edge Dispatcher.

Figure 8:
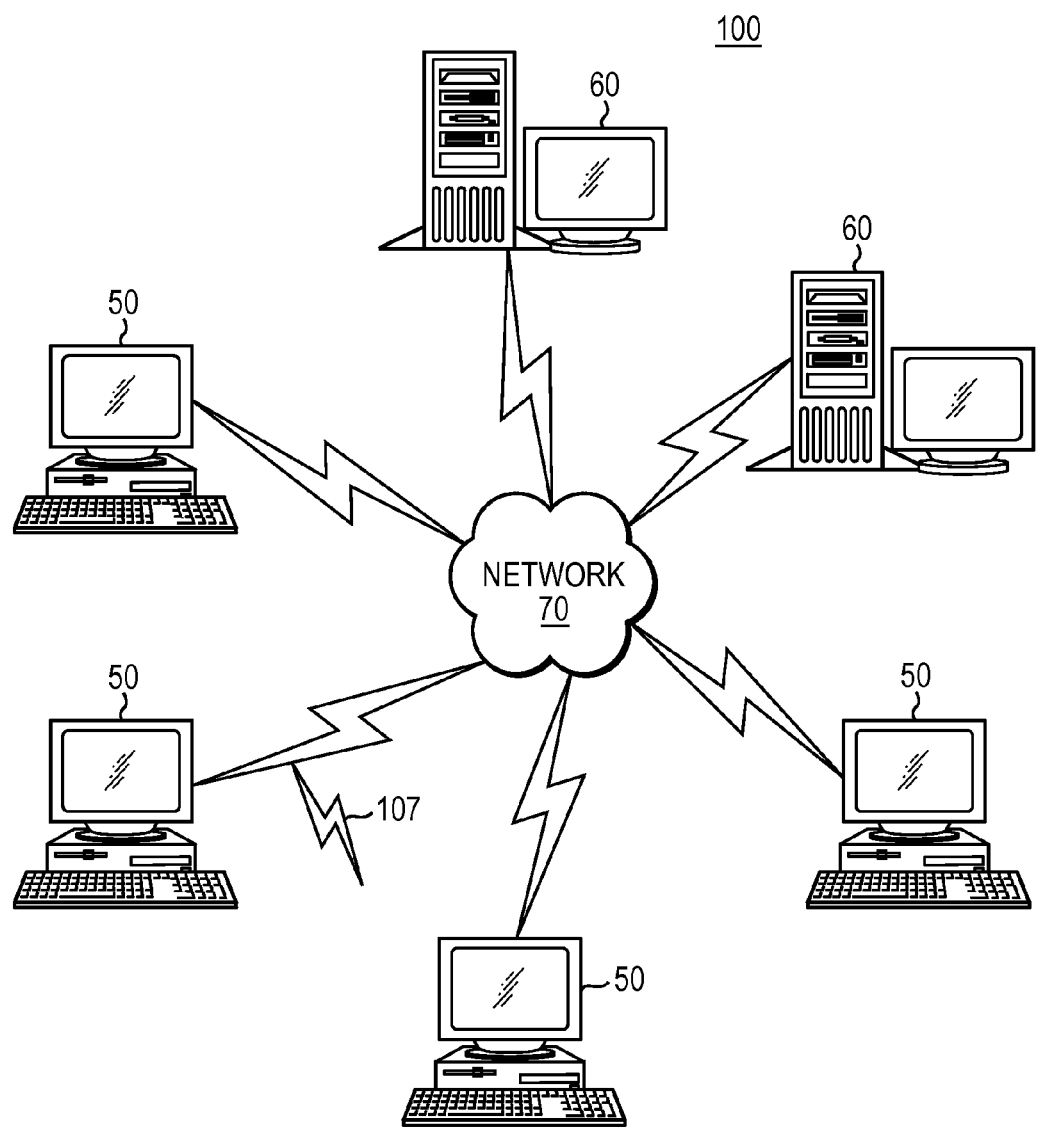

FIG. 8 is a schematic view of a computer network environment in which embodiments of the invention are deployed.

Figure 9:
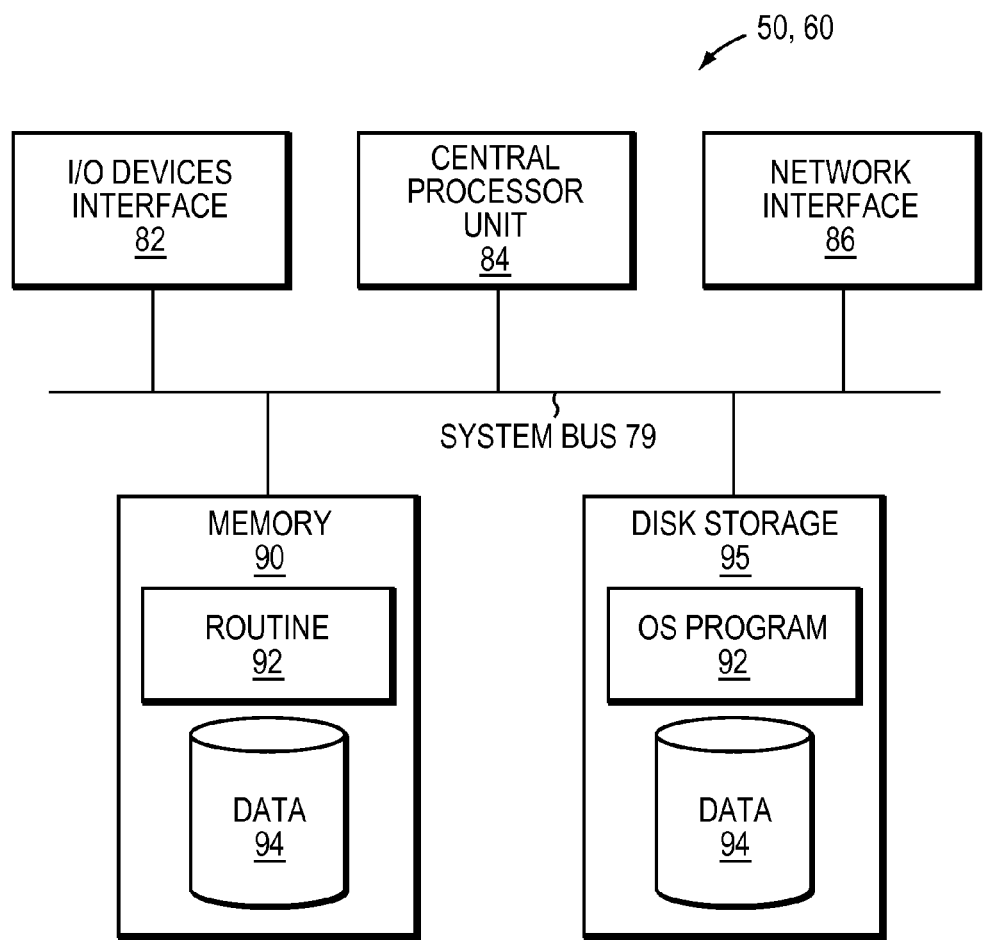

FIG. 9 is a block diagram of a computer node of the network of FIG. 8.

DESCRIPTION OF THE INVENTION

Elements of the invention include several combinations of study data structures and node types. There are roughly six types of study data structures: Preview Study, Detailed Study, Study Review Request, Study Review Acceptance, Study Review Cancellation, Study Review. The node types include two primary node types and two router node types: Consuming Node, Originating Node, Edge Dispatcher, and Global Dispatcher.

Preview Study

The first of the five major data structures is the Preview Study (FIG. 1-110), which contains one or more samples of the study images which provide a survey of the study images, combined with both image and patient metadata. The preview study is intended to provide sufficient data to make a decision on further routing of the review request, or enable a decision on whether to fulfill (accept) a review request.

Detailed Study

The second major data structure is the Detailed Study (FIG. 1-120), which consists of one or more progressively-rich resolution images combined with additional metadata. A set of preferred embodiments is to provide access to a plurality of image tiles or a stream of image tiles providing on-demand access to regions (x, y, & z locations and magnification) of the images as they are viewed by the consuming node. A second preferred embodiment is to push or pull the entire image from the originating node to the consuming node, caching the image for future consumption. The metadata may also be realized in a progressive manner, by providing on-demand access to additional patient metadata that is related to but not contained within the study itself (such as but not limited to additional patient history, results of previous pathology studies, non-pathological study results, detailed studies other than the current study).

Study Review Request

The third major data structure is the Review Request (FIG. 1-130), which contains the Preview Study, a reference to the Detailed Study, as well as addressing and routing information, and any policies and constraints on the study, such as (but not limited to) priority, expiration, expiration after acceptance, reimbursement rates, and number of authorized reviews.

Study Review Acceptance

The fourth major data structure is the Study Review Acceptance, equivalently acceptance message (FIG. 1-140), which is returned by the consuming node to the originating node in response to a Review Request and Preview Study. The acceptance message signals either the acceptance or rejection of the review request by the consuming node. In the event of an acceptance message, if the review request included a plurality of consuming nodes, if the review request's cardinality (number of requested reviews) has been met, a "broadcast acceptance" message is sent to all remaining consuming nodes. This message signals that the review request has been conditionally fulfilled and that no additional acceptance messages will be processed for the review request. In a preferred embodiment, the Preview Study remains cached on the consuming node for the duration of the contention lock of the review request acceptance. If the lock expires, the Review Request is once again forwarded to the remaining recipients for processing.

Study Review Cancellation

The fifth major data structure is the Study Review Cancellation message (FIG. 1-150), which is sent by the originating node or a dispatcher. The Study Review Cancellation message is sent in response to a number of circumstances, including but not limited to: cancellation of the review request by the originating, expiration of lease time for a review, meeting the cardinality of a review request in a Multiple Consumer Review Request (FIG. 6).

Study Review

The final major data structure is the Review (or Diagnosis) (FIG. 1-160) which is returned by the consuming node to the originating node, which may contained a detailed written or audio diagnosis, a series of annotations (x, y, & z locations, zoom factors and notations) or images, as well as review metadata, which may contain, but is not limited to, physician metadata, review date & time, duration of review, and detail of what elements of the Detailed Study were consumed.

Originating Node

Originating nodes, equivalently originator nodes (FIG. 2-210), are the end-points which allow for the creation of Preview Studies, Detailed Studies and Review Requests. Originating nodes address the study to one or more consuming nodes for review. Originating nodes also process Reviews generated by consuming nodes in response to a Review Request. In a preferred embodiment, the originating node coordinates with an edge dispatcher to route the study to the intended consuming nodes.

Consuming Node

Consuming nodes, equivalently consumer nodes (FIG. 2-220), process review requests, preview studies and detailed studies to provide a review to an originating node. Consuming nodes initially receive Preview Studies enabling a study to be accepted or rejected. If accepted, the consuming node communicates that acceptance (generally through an edge dispatcher), and receives the Detailed Study for review. Once a Review has been created, the Review is committed to the originating node. In the preferred embodiment, the consuming node coordinates with an edge dispatcher to route these data structures to the originating node. When a consuming node accepts or rejects a review request, this acceptance or rejection is signaled to the originating node. In a preferred embodiment, this signaling is routed through a plurality of dispatchers.

Edge Dispatcher

The edge dispatcher (FIG. 2-240) node belongs to a single organization. If an originating node exists within the organization, the edge dispatcher is responsible for addressing and routing studies which originate within the organization to the appropriate consuming organization's edge dispatcher for review. If a consuming node exists within the organization, the edge dispatcher receives and manages the queue of studies to be reviewed by the organization's consuming node. In both cases, the edge dispatcher handles studies from internal and external organizations in the same manner, merging both local review requests and review requests from external organizations which are intended for the consuming node (FIG. 3).

Global Dispatcher

In networks involving more than a handful of peer organizations, a more complex network topology is required. To directly connect the edge dispatcher of an organization in the network to every other edge dispatcher in the network becomes labor intensive as the network grows. Having central nodes for the edge dispatchers to connect to facilitates the management of the members of the network, and allows for improved reliability through having multiple central nodes, providing multiple paths to organization. Such central nodes are called Global Dispatchers.

The exchange of studies is accomplished through a connection of a plurality of organization nodes with a Global Dispatcher node. The Global Dispatcher node facilitates the connection of new organizations to the cloud and facilitates the directed exchange of studies to the intended recipients. The network of Organizations connected to a Global Dispatcher is referred to as a cloud, or a pathology network. The Global Dispatcher facilitates the exchange of studies through the authentication and federation of a new organization into the cloud, obviating the need to exchange authentication information with all organizations which currently exist in the system on an individual basis.

The global dispatcher (FIG. 2-250) node manages the transfer of data structures between edge dispatchers, and federates the edge dispatchers and organizations. The global dispatcher's primary function is to receive study data structures, routing them to the edge dispatcher of a plurality of recipients. When a review request is accepted by a consuming node, the Global Dispatcher generates a 'broadcast acceptance' to both the originating node as well as to all additional addressed consuming nodes of the study. The Global Dispatcher queries the required security credentials for the Detailed Study from the originating node, conveying them to the consuming node, providing access to the Detailed Study through a plurality of means, either directly or through one or more dispatcher nodes.

Discussion of Node & Network Topologies

The digital pathology system from which the study originates is termed the originating node. Likewise, the digital pathology system receiving the study and providing a review is termed the consuming node. The nodes themselves are considered to have one or more networked computational units having a variety of designs.

A networked computational element is an addressable endpoint in a network that can perform a computational task. The endpoint, or node, may be simply a networked computer, a cluster of networked servers, a virtual server within a pooled set of server resources, one of a set of virtual servers contained on a server, or any combination of hardware and software that is able to provide a network address along with execution of the digital pathology system's processing described in this invention.

A digital pathology system is a demarcated set of networked computational elements under the administration of a single organization. When the originating node and consuming node are collocated within a single digital pathology system, this is termed an Intra-site digital pathology system, or simply Intra-site. When the originating node and consuming nodes each belong to separate digital pathology systems, and therefore belong to different organizations, this topology is termed an Inter-site digital pathology system, or simply Inter-site. One characteristic difference between Intra-site and Inter-site is the network topology. Intra-site will tend to have geographically co-located networked computational elements, and dedicated high speed connections between geographically disparate networked computation elements. Inter-site network topologies will tend to have more ad hoc connections that would utilize combinations of non-dedicated or on-demand network infrastructures, typically resulting in a less controlled, more variable performance relative to the Intra-site network topology, which generally utilizes more over-provisioned and controlled resources.

In a preferred embodiment, an Intra-site Network Topology is utilized, with both the originating node and the consuming node within the same organization (site). A study is created by the organization's originating node, addressed to the organization itself, and is reviewed by the organization's consuming node, and is generally routed through and queued by a local edge dispatcher. Without loss of generality, the originating and consuming nodes may exist on the same LAN or WAN, or may be connected via VPN or other tunneling technologies.

In a second preferred embodiment, an Inter-site Network Topology is utilized, with the originating node and the consuming node within different organizations (sites). A study is created by one organization's originating node, addressed to a second organization, and is reviewed by the second organization's consuming node, generally routed through a plurality of edge and global dispatcher nodes. Without loss of generality, the two organizations may be connected to one another via a dedicated circuit, VPN, the Internet or any other network technologies. Both of these Intra-site and Inter-site embodiments have further embodiments allowing a plurality of network topologies between an originating and consuming organization, spanning multiple Intra-site and Inter-site networks in order to properly route and deliver a request for review to the consuming organization. This plurality of networks and organizations comprises today's hospitals, clinics, private practices and expert centers, as well as future organization types such as a healthcare cooperatives and virtual practices.

Discussion of Organizations

An organization (FIG. 2-230) is a logical entity representing an originator, a consumer, or an originator and consumer of studies.

Examples of an organization that acts as an originator (FIG. 2-231) would be a clinic or private practice unable to provide pathology services or hospital without a particular subspecialty. An organization acting as an originator contains an Originating Node (210) and an Edge Dispatcher Node (240).

Examples of an organization that only acts as a consumer (FIG. 2-232) would be an expert center or virtual practice. An organization acting as a consumer contains a Consuming Node (220) and an Edge Dispatcher Node (240).

Examples of an organization which is both an originator and a consumer (FIG. 2-233) would be a large clinic or hospital providing all subspecialties. Such an organization would contain an Originating Node (210), a Consuming Node (220) and an Edge Dispatcher Node (240).

An originating organization generates studies and review requests, and a consuming organization fulfills review requests. In the preferred embodiment the organization is able to both originate and consume studies, and contains both an originating node and a consuming node. The preferred embodiment of any of these systems also includes an edge dispatcher to facilitate the queuing and routing of review requests from the originating node to the consuming node.

Discussion of Dispatchers & Embodiments

The present invention introduces two logical elements into the digital pathology systems for the purpose of controlling and synchronizing the flow of data among the digital pathology systems' networked computational elements. These two logical elements are termed dispatchers; there is both an edge dispatcher and a global dispatcher. The edge dispatcher is responsible for dispatching services for a discretely isolated digital pathology system, and this dispatcher is used to demarcate that system. An edge dispatcher may be connected to a peer edge dispatcher, or may be connected through a global dispatcher to a plurality of edge dispatchers. The global dispatcher provides similar functionality as the edge dispatcher with additional functionality required to coordinate between and federate two or more edge dispatchers. Once an edge dispatcher node is connected to a global dispatcher node, that edge dispatcher may address and route review requests to all nodes directly or indirectly connected to the global dispatcher node.

In one embodiment, an originating organization contains at least an edge dispatcher and either an originating node or a consuming node.

Another embodiment includes a digital pathology solution where the originating node provides the preview study, review request and detailed study directly to the consuming node, and receives study acceptance and diagnosis directly from the consuming node (FIG. 7-710). In a set of further, non-limiting embodiments, an edge dispatcher may be added to route and queue all of the aforementioned data structures (FIG. 7-720), and a global dispatcher may be added to both route and queue all of the data structures between edge dispatchers (FIG. 7-740). Additionally, one or more of the data structure paths may be designed to bypass one or all of the intermediate routing nodes, as exemplified by the direct distribution of the detailed study from originator to consumer, bypassing the first the edge dispatcher (FIG. 7-730), and likewise bypassing both edge dispatchers and the global dispatcher (FIG. 7-750).

When an organization containing an originating node is connected to external dispatchers, that node has joined an Inter-site Network Topology. The organization may act as an originator of studies to both its own organization and any other organization with a dispatcher that is connected via any series of connections.

When an organization containing a consuming node is connected to external dispatchers, that node has joined an Inter-site Network Topology. That organization may now act as a consumer of studies both from its own organization and from any other organization with a connected dispatcher. In this case, an edge dispatcher located within the same organization as the consuming node is used to route and queue both local and external review requests to the consuming node (FIG. 3).

One embodiment of the invention is a means of processing study review requests through a federated system of dispatch nodes through the inclusion of a Global Dispatcher, which is connected to a plurality of edge dispatchers. Such routing facilitates routing a large numbers of review requests over constrained networking infrastructure (constrained in bandwidth, security, information privacy) with little or no user intervention. The Global Dispatcher node enables the addressing and distribution of studies from an originating node to one or more receiving nodes. The method further comprises the addressing, routing, and transactional queue management of a plurality of user nodes and dispatcher nodes. The present invention allows a plurality of interconnected Organizations, which are equivalently referred to as organization nodes, to combine with expert centers representing many of the major hospitals around the world for the purpose of providing Pathology Reviews. Organization nodes with requirements for a second opinion or an expert opinion on a study, possibly from an expert center having been defined as accepting studies requiring a subspecialty diagnostic service that is not provided by locally represented work nodes will provide an option of selecting the required service from any connected organization node, physician node, or Virtual Practice federation of nodes.

Through the addressing and routing of study data to multiple qualified organization nodes (FIG. 6) within the cloud, the originating organization node increases the redundancy of destination nodes that can fulfill the requested study review service. Further, the latency of service fulfillment is potentially decreased by multiple service request submissions. Organization nodes can be defined as qualified though a process of vetting. The vetting process provides for the inclusion and summary of user supplied analysis. In one embodiment, the criteria are derived from the criteria hospitals uses for non-digital second opinions and referrals. By addressing the study service request to a set of two or more qualified organization nodes, the qualified organization node with a status indicating it is has available resources will be requested at a higher priority to respond and provide a diagnostic service. The set/collection may contain any combination of individual nodes, organization nodes or virtual practice nodes from the cloud dispatcher. When the study is assigned to the collection, all consuming nodes that are addressed for receipt, receive notifications of the assignment for service fulfillment.

Subsequent to the Review Request, the study is rendered in a viewable state in the consuming node's available work queue. The first consuming node to indicate that review service has been completed and that the acceptance state of the work order has been set for the study will cause the consuming node to perform a method that will remove the case from the other consuming nodes' available queues. Subsequently, the originating organization node will receive notification that the study is now in an accepted state, along with data indicating the organizational node that accepted the study. The consuming node that sets the study in the accepted state creates a contention lock that includes an expiration time. This time indicates how long the consuming node will retain the lock on the acceptance state of the study. Further, the lock provides an exclusive time period during which the consuming node will be able to review the study and commit a review by submitting the diagnosis, annotations and additional references back to the originating node. Upon completion of these processes, the study will be marked as being in a completed state. If the lock expires prior to the notification that the diagnosis data is set, the study will be returned to the available work queue for all consuming nodes.

In order to ensure that individual nodes, virtual practice nodes, and organization nodes are associated with the highest possible quality of service, various metrics and ratings data may be recorded. These metrics are provided, in one embodiment, by system users, specifically doctors associated with the organization nodes. Ratings may include the service fulfillment time which is calculated as the time from acceptance to committing a diagnosis. Additionally the ratings may include the number of expired cases, the viewed spatial extent of the image, viewing resolutions, and peer quality ratings of the diagnoses (agree/disagree with diagnosis, quality of diagnosis write-up). A process is defined that utilizes the ratings in order to define an individual node or organization node as being excluded from a recipient list. In one embodiment, a particular individual node or organization node may be rated as providing unsatisfactory diagnoses or repeatedly accepts and subsequently allows a study to expire, and/or delaying the workflow of a study beyond a predefined study time review limit.

Virtual Practices

Virtual Practices are a specific embodiment of a Consuming Organization (232) consisting of one or more physicians (Consuming Nodes). The Virtual Practice is created within a Cloud Pathology Network. Virtual Practice nodes may have defined a data attribute indicating if the node can service specific or general subspecialty care requests. Such a Virtual Practice node will generally be made up of expert nodes corresponding to specific field services or subspecialty services. When implemented in a cloud computing environment, the advertised field information provides a means for the node to promote itself as being defined as the node having the attribute of being the primary or secondary node for dispatching at a higher priority than similar nodes.

Virtual practice organizations are logical organizations consisting of one or more originating or consuming nodes which exist beyond a physical location, sharing a single edge dispatcher. Whereas most expert centers and hospitals have a single physical presence, a virtual practice consists of a plurality of physically distributed originating or consuming nodes, whose relationship is only defined in that they are connected through a common edge dispatcher. The collection of the originating or consuming nodes through the dispatcher defines an organization which offers or requires services to the network and which may generate Review Requests to the network, or to which Review Requests may be addressed. In one embodiment, a virtual practice may be labeled as a premium or subspecialty expert organization node. In another embodiment, a virtual practice may be labeled as servicing cost constrained review requests, or deferring cost in conjunction with research. In all embodiments, Virtual Practices are created by combining individual nodes or organization nodes, such as a network of affiliated organizations (e.g., a group of affiliated hospitals). The individual nodes or organization contained within a Virtual Practice Node define a self-policing service group, which are responsible for enforcing their own membership policies and metrics. Note that the mentioned service group is not required to map to organization node boundaries, and controls its own constituency.

Virtual Practice Nodes

In the cloud dispatcher scenario, virtual practice nodes can be defined as providing a specialty service to the organizations within the cloud. In one embodiment, group nodes may be labeled as premium or subspecialty expert group nodes. The virtual practices may further be labeled as discounted cost or pro-bono group nodes. In yet another embodiment, group nodes are created by individual nodes or organization nodes. The individual nodes or organization nodes define a self-policing service group. Note that the mentioned service group is not required to map to organization node boundaries.

In one embodiment, an expert group node is defined as a type of virtual practice node containing nodes that have a common subspecialty label. The expert groups allow the addition of expert level member nodes. As they are providing expert level services, they must also be self-policing, to make sure that all members are providing the quality of diagnostic service that they can market, in order to be the expert group of choice for a subspecialty.

In one embodiment, discounted service group nodes are defined as a collection of nodes provided as an optional node providing services for organization nodes that are defined with labels that indicate 'price sensitive' state or 'less comprehensive insurance' state or 'reimburses at a lower rate' state. In a further embodiment, Pro-bono service group nodes are defined in order to provide a patient screening method using predefined qualifying metrics to disable service fulfillment.

Lifecycle of a Study

In any embodiment of a pathology system, there exists both a study originator and a study consumer. Between these two nodes there exists a series of exchanges which provide progressive access to both image and metadata of the study, often times facilitated by one or more dispatchers.

In one simple embodiment (FIG. 5-M*essage* Exchange for a Single Consumer Review), demonstrating the data communication and transformation between a single originator and a single consumer, there exists a single originating node (210) and a single consuming node (220) connected through a single edge dispatcher (240). The initial input is the creation of a study (both Preview Study (110) and Detailed Study (120)) by an originating node, followed by the creation of a review request (130), addressing the study to the consuming node. All three of these structures exist on the originating node (110), and following the addressing instructions contained within the Review Request, the Request (containing the Preview Study) would be routed from the Originating Node through the Edge Dispatcher (530) to the Consuming Node (520). Upon receiving the review request, the consuming node evaluates the review request and the associated preview study, to determine the type of Acceptance Message (140) to be sent. Rejection of the Review Request would result in a Acceptance Message (140) signaling a rejection being sent by the consuming node (220) to the edge dispatcher (240), which would then be forwarded to the originating node (210). A Rejection message terminates that consuming node's (220) involvement in the current Review Request. The alternative is that the consuming node (220) accepts the Review Request, resulting in an acceptance message (140) to the Edge Dispatcher (240), who in turn forwards the message to the originating node (210). The acceptance message includes necessary security tokens to enable secure access to the Detailed Study (120) (via the edge dispatcher). The consuming node accesses the desired images and metadata in a progressive manner until a diagnosis can be made, at which point, a Review message (160) from the consuming node (220) is sent, through the edge dispatcher, to the originating node (210). This action also concludes that consuming node's (220) involvement in the Review Request and the Review is complete.

Extensions of this simple embodiment include but are not limited to sending one or more of the messages directly from one end node to another (FIGS. 7-730 and 7-750) as compared to all messages being routed through a dispatcher (FIGS. 7-720 and 7-740), as well as including a plurality of edge and global dispatchers in the communications process (FIGS. 7-740 and 7-750).

An additional embodiment is when an originating node generates a Review Request addressed to one or more of a plurality of qualified consuming (FIG. 6). Through the addressing and routing of a Review Request to multiple qualified consuming nodes, the latency of service fulfillment is decreased, as it will be fulfilled by the first consuming node with available resources. When the number of consuming nodes providing a review fulfills the cardinality requirements of the review request (in FIG. 6, where one review is requested, when the first consuming node accepts), the review request is fulfilled, and a Study Review Cancellation message (150) is sent to the remainder of Consuming Nodes. In this manner, the originating node may increase redundancy and speed of review by addressing the review request to a plurality of consuming nodes.

Simple Distribution Process

In a preferred embodiment of the Simple Distribution Process (FIG. 7-710), the initial request for Study review is initiated by the Originating Node signaling the Consuming Node, indicating the presence of an available study on the Originating Node.

This embodiment is a computer-based method of distributing biological sample data based on specified study review criteria, both of which are on the Originating Node (FIG. 7-710-210). On the Originating Node, a Study (FIG. 1-105) is generated based on the specified study review criteria. Further, a progressive transmission is prepared. The progressive transmission is based on transmission of requested subsets of biological sample data, thereby not requiring the whole of the data to be transmitted. Additionally, based on the specified study review criteria, a Study Review Request (FIG. 1-130) is prepared. The review request is then transmitted (FIG. 7-710-130) to at least one Consuming Node (FIG. 7-710-220). In response to a signal from the Consuming Node, the transmission is streamed (FIG. 7-710-120) in a progressive manner, as a subset, in part or in full, from the Originating Node to the Consuming Node. These subsets are based on the progressive technique employed, and would include the following non-limiting aspects: spatial regions, scale, tiling, or other common progressive image transmission techniques.

Figure 1:
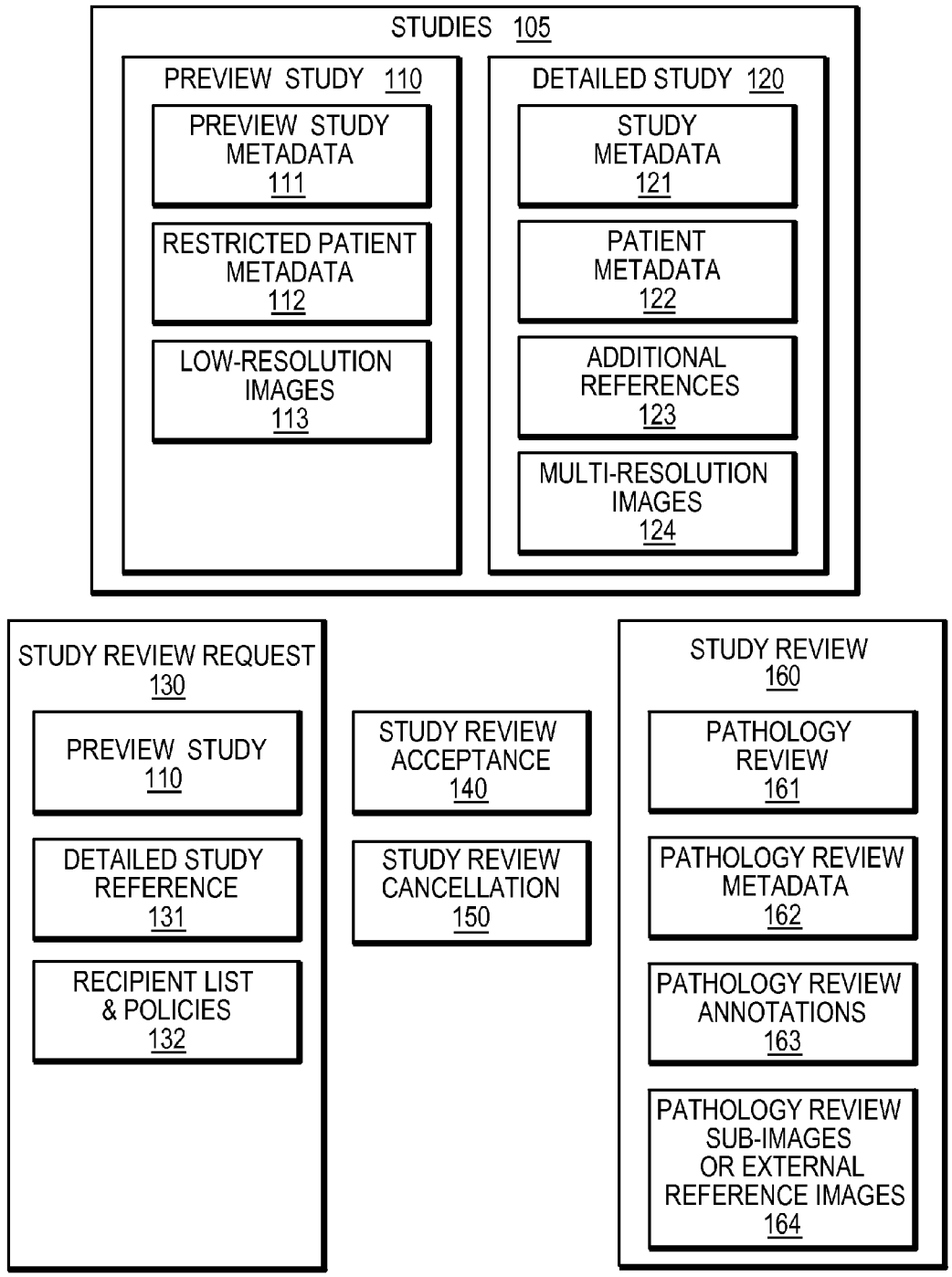
FIG. 1

A further embodiment based on the Simple Distribution Process includes specific data in the Study Review Request. This non-limiting embodiment includes the Patient Metadata (including patient history, specifics of the current study) (FIG. 1-112 & 1-122), preparation data, and/or image capture specifications (FIG. 1-121) in the Study Review Request (FIG. 1-130). A yet further embodiment would optionally include the following data in the Study Review Request as well (FIG. 1-132): the study request type, the cardinality of request, the time of request, the expiration time of request, a request reimbursement specification, and/or a subspecialty requirements for study review.

In yet a further embodiment of the Simple Distribution Process, the progressive transmission can also be followed by a Study Review (FIG. 5-160) being transmitted from the Consuming Node (FIG. 2-220) to the Originating Node (FIG. 2-210), the Study Review containing information based on a review of the study performed at the Consuming Node. Additionally, the information contained in the Study Review can specifically be defined as one or more of the following data (FIG. 1-162): study review quality control parameters, image quality assessment information, structural analysis report, morphological analysis report, quantitative analysis report. Further, the diagnosis can optionally contain (FIG. 1-161): a diagnosis, determination of pathological condition, a description of the diagnosis, and one or more of the following: additional text, audio commentary, and/or video commentary. There is a further embodiment where the Study Review includes derived images (FIG. 1-164) and metadata including: the metrics of tissue characteristics, spatial bounds for regions of interest, and the results of geometric analysis. The results of geometric analysis including one or more of the following: gradient analysis, morphological analysis, edge/curve detection, and texture analysis.

Dispatched Distribution Process

In a preferred embodiment of the Dispatched Distribution Process (FIG. 7-720), the initial request for Study review indicating the presence of an available study on the Originating Node, is initiated by the Originating Node signaling a Dispatcher Node, which forwards the communications to the Consuming Node.

This embodiment is a computer-based method of distributing biological sample data based on specified study review criteria, both of which are on the Originating Node (FIG. 7-720-210). On the Originating Node, a Study (FIG. 1-105) is generated based on the specified study review criteria. Further, a progressive transmission is prepared. The progressive transmission is based on transmission of requested subsets of biological sample data, thereby not requiring the whole of the data to be transmitted. Additionally, based on the specified study review criteria, a Study Review Request (FIG. 1-130) is prepared. The review request is then transmitted (FIG. 7-720-130) to at least one Dispatcher Node (FIG. 7-720-240). The Study Review Request is then forwarded from the Dispatcher Node to a Consuming Node (FIG. 7-720-220). In response to a signal from the Consuming Node, which is sent to the Dispatcher Node and forwarded to the Originating Node, the transmission is sent (FIG. 7-720-120) in a progressive manner, as a subset, in part or in full, from the Originating Node to the Consuming Node via the Dispatcher. These subsets are based on the progressive technique employed, and would include the following non-limiting aspects: spatial regions, scale, tiling, or other common progressive image transmission techniques.

As a further embodiment of the Dispatched Distribution Process, the Dispatch Node is comprised of: a computer network that in sum is able to provide the equivalent external functionality of the Dispatch Node.

As a further embodiment of the Dispatched Distribution Process, the transmissions to the Dispatch Node include secure communications comprising: authentication of the Originating Node, and authentication of the Consuming Node.

As a further embodiment of the Dispatched Distribution Process, the Dispatch Node provides differential services to a plurality of Originating Nodes and Consuming Nodes. These services comprising the following in a non-limiting manner: a prioritization of request fulfillment based on specified priority, and/or sequencing of requests based on defined workflow rules.

As a further embodiment of the Dispatched Distribution Process, signaling and transmitted data may be routed through the Dispatcher or directly from a Originating Node to a Consuming Node (FIG. 7-730).

As a further embodiment, the data structures and signaling may be transmitted through a plurality of Dispatcher Nodes (FIGS. 7-740 & 7-750).

FIG. 8 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

FIG. 9 is a diagram of the internal structure of a computer (e.g., client processor/device 50 or server computers 60) in the computer system of FIG. 8. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 8). Memory 90 provides volatile storage for computer software instructions 92 and data 94 used to implement an embodiment of the present invention (e.g., digital pathology system operators/engines including pathology study exchange process modules and nodes, and supporting code detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-based method of providing a pathology study exchange, comprising:
    generating a request for review of a Study of a biological sample based on Study Review Criteria of an Originating Node,
    said generating including preparing a progressive image transmission form of the biological sample data;
    addressing the generated study review request to one or more qualifying Consuming Nodes, said addressing notifying the one or more qualifying Consuming Nodes of the generated Study Review Request addressed for assignment for one of the qualifying Consuming Nodes to accept and fulfill review of the study;
    for each of the one or more qualifying Consuming Nodes, rendering the study in a viewable state a work queue of in the qualifying Consuming Node;
    in response to one of the qualifying Consuming Nodes accepting the study for review, (i) removing the study from the other qualifying Consuming Node's work queues, (ii) creating a contention lock on acceptance state of the study, the contention lock includes an expiration time and providing an exclusive time period in which the one qualifying Consuming Node is to review the study and submit a study review to the originating Node, and (iii) transmitting the study from the Originating Node to the one qualifying Consuming Node, including the progressive image in part or in full form;
    upon the one qualifying consuming node submitting the study review to the Originating Node, marking the study as being in a completed state, where if the contention lock expires prior to the one qualifying Consuming Node submitting the study review then returning the study to the work queues of the one or more qualifying Consuming Nodes.

2. A method as claimed in claim 1, wherein the generated study Review Request includes one or more of the following data:
    patient metadata, preparation data, image capture specifications, image metadata.

3. A method as claimed in claim 1, wherein the Originating Node and at least one of the qualifying consuming nodes are remote from each other; and
    wherein the generated study Review Request additionally includes one or more of the following data:
    review request type, cardinality of request, time of request, expiration time of request, request reimbursement specification, subspecialty requirements for study review.

4. A method as claimed in claim 1, wherein the work queue of a qualifying Consuming Node may contain internal study Review Requests and external study review requests, wherein an external study Review Request is generated by a different organization
from the Consuming Node such that the study co-exists in a work queue of an organization of the Originating Node and in a work queue of the organization of the Consuming Node.

5. A method as claimed in claim 4, wherein the qualifying Consuming Nodes represent hospitals and expert centers providing pathology review services, and the
study review criteria of the Originating Node includes a second opinion or an expert opinion on the study and a diagnosis.

6. A method as claimed in claim 1, wherein the study review includes:
review metadata having an indication of physician, date and time of review and duration of review; and
diagnosis by a user of the submitting qualifying Consuming Node, wherein the diagnosis comprises:
determination of pathological condition, and
a description of the diagnosis, and
one or more of the following: additional text, audio commentary, video commentary and annotation at a specific image location and resolution.

7. A method as claimed in claim 1, wherein rendering the study in the qualifying Consuming Node's work queue includes
prioritizing review fulfillment based on priority specified with the study and sequencing of study review requests based on defined workflow rules.

8. A computer-based method of providing a pathological study exchange, comprising:
generating a request for review of a Study of a biological sample based on Study Review Criteria of an Originating Node, said generating includes preparing
a progressive image transmission form of the biological sample data;
addressing the generated study review request to one or more qualifying Consuming Nodes, said addressing notifying the one or more qualifying Consuming Nodes of the generated Study Review request, addressed for assignment for one the qualifying Consuming Nodes to accept and fulfill review of the study by:
transmitting the Study Review Request from the Originating Node to at least one Dispatcher;
signaling the Study Review Request from each Dispatcher to respective ones of the qualifying Consuming Nodes;
signaling from the qualifying Consuming Nodes to request Study transmission from respective Dispatchers; and
signaling the Study transmission request from the respective Dispatchers to the Originating Node;
in response to one of the qualifying Consuming Nodes accepting the study for review, (i) removing the study from the other qualifying Consuming Node's work queues, (ii) creating a contention lock on acceptance state of the study, the contention lock includes an expiration time and providing an exclusive time period in which the one qualifying Consuming Node is to review the study and submit a study review to the originating Node, and (iii) transmitting the study from the Originating Node to the one qualifying Consuming Node through respective dispatchers, including the progressive image in part or in full form; and
upon the one qualifying consuming node submitting the study review to the Originating Node, marking the study as being in a completed state, where if the contention lock expires prior to the one qualifying Consuming Node submitting the study review then returning the study to the work queues of the one or more qualifying Consuming Nodes.

9. A method as claimed in claim 8, wherein the at least one Dispatcher is comprised of: a computer network.

10. A method as claimed in claim 8, wherein said signaling and said transmitting through Dispatchers include secure communications comprising: authentication of the Originating Node, and authentication of respective qualifying Consuming Node.

11. A method as claimed in claim 8, wherein the at least one Dispatcher provides differential services to a plurality of Originating Nodes and qualifying Consuming Nodes, services comprising: a prioritization of study review request fulfillment based on specified priority, and sequencing of study review requests based on defined workflow rules.

12. A method as claimed in claim 8, wherein transmitting the Study in part or in full form includes transmitting the study from the Originating Node to the at least one Dispatcher, and then from the at least one Dispatcher to the one qualifying Consuming Node.

13. A method as claimed in claim 8 wherein the Originating Node and at least one of the qualifying Consuming Nodes are remote from each other.

14. A method as claimed in claim 8 wherein the work queue of a qualifying Consuming Node may contain internal study Review Requests and external study review requests, wherein an external study Review Request is generated by a different organization from the Consuming Node such that the study co-exists in a work queue of an organization of Originating Node and in a work queue of the organization of the Consuming Node.

15. A method as claimed in claim 14 wherein the qualifying Consuming Nodes represent hospitals and expert centers providing pathology review services, and the study review criteria of the Originating Node includes a second opinion or an expert opinion on the study and a diagnosis.

16. A method as claimed in claim 8 wherein the study review includes:
review metadata having an indication of physician, date and time of review and duration of review; and
diagnosis by a user of the submitting qualifying Consuming Node, wherein the diagnosis comprises:
determination of pathological condition, and
a description of the diagnosis, and
one or more of the following: additional text, audio commentary, video commentary and annotation at a specific image location and resolution.

* * * * *